United States Patent [19]

Burns et al.

[11] Patent Number: 4,852,989
[45] Date of Patent: Aug. 1, 1989

[54] BLEACHING COMPOUNDS AND COMPOSITIONS COMPRISING FATTY PEROXYACIDS SALTS THEREOF AND PRECURSORS THEREFOR HAVING AMIDE MOIETIES IN THE FATTY CHAIN

[75] Inventors: Michael E. Burns, West Chester, Ohio; Frederick E. Hardy, Newcastle upon Tyne, England

[73] Assignee: The Procter & Gamble Company, Cincinnati, Ohio

[21] Appl. No.: 47,804

[22] Filed: May 8, 1987

[51] Int. Cl.$^4$ .................. C07C 179/10; C07C 179/20; C11D 3/39; D06L 3/02

[52] U.S. Cl. ............................. 8/107; 8/111; 252/102; 252/186.38; 252/186.39; 252/186.42; 548/312; 548/341; 560/21; 560/41; 560/43; 560/155; 562/430; 562/443; 562/556; 562/561; 562/2; 562/41; 562/44; 562/52; 562/887; 564/98; 564/99; 564/153; 564/155

[58] Field of Search ............... 8/110, 107; 260/502 R, 260/507 R, 513 R, 502.6, 546; 252/94, 95, 98, 102, 186.23, 186.42, 186.38, 186.39; 564/153, 98, 155, 99, 159; 560/41, 130, 21, 43, 155; 548/341, 312; 562/443, 561, 556, 430

[56] References Cited

U.S. PATENT DOCUMENTS

| | | | |
|---|---|---|---|
| 3,751,370 | 8/1973 | Stimberg et al. | 252/102 |
| 4,225,577 | 9/1980 | Tilly et al. | 424/5 |
| 4,283,301 | 8/1981 | Diehl | 252/102 |
| 4,443,623 | 4/1984 | Photis | 560/170 |
| 4,444,674 | 4/1984 | Gray | 252/95 |
| 4,525,292 | 6/1985 | Cushman et al. | 252/102 |
| 4,536,314 | 8/1985 | Hardy et al. | 252/102 |
| 4,539,130 | 9/1985 | Thompson et al. | 252/94 |
| 4,623,729 | 11/1986 | Natarajan et al. | 546/256 |
| 4,634,551 | 1/1987 | Burns et al. | 252/102 |
| 4,671,891 | 6/1987 | Hartman | 252/186.42 |
| 4,681,592 | 7/1987 | Hardy et al. | 8/111 |
| 4,686,063 | 8/1987 | Burns | 252/102 |

FOREIGN PATENT DOCUMENTS 0105689 4/1984 European Pat. Off. .

OTHER PUBLICATIONS

Pending U.S. patent application Ser. No. 907,207, Burns, filed 9/12/86.

*Primary Examiner*—Dennis Albrecht
*Assistant Examiner*—Ron Krasnow
*Attorney, Agent, or Firm*—Robert B. Aylor; Donald E. Hasse; Thomas H. O'Flaherty

[57] ABSTRACT

This invention relates to bleaching compounds and compositions that provide effective and efficient surface bleaching of textiles over a wide range of bleach solution temperatures. The bleaching compounds of the invention yield a peroxyacid with a polar amide link in the hydrophobic chain when used in the bleaching compositions. In a preferred embodiment, the bleaching compositions of the invention are also detergent compositions.

19 Claims, No Drawings

BLEACHING COMPOUNDS AND COMPOSITIONS COMPRISING FATTY PEROXYACIDS SALTS THEREOF AND PRECURSORS THEREFOR HAVING AMIDE MOIETIES IN THE FATTY CHAIN

BACKGROUND OF THE INVENTION

Technical Field

This invention relates to very stable peroxygen bleaching compositions and processes therefor that provide effective bleaching of textiles over a wide range of temperatures.

SUMMARY OF THE INVENTION

The present invention relates to a bleaching compound providing a peroxyacid of the following general formulas:

$$R^1-\underset{\underset{O}{\|}}{C}-\underset{\underset{R^5}{|}}{N}-R^2-\underset{\underset{O}{\|}}{C}-OOH \text{ or } R^1-\underset{\underset{R^5}{|}}{N}-\underset{\underset{O}{\|}}{C}-R^2-\underset{\underset{O}{\|}}{C}-OOH$$

wherein each $R^1$ is an alkyl, aryl or alkaryl group containing from about 1 to about 14 carbon atoms, each $R^2$ is an alkylene group with at least one double bond alpha, beta or either one or both of the percarbonyl group and the amide carbonyl group and containing from 2 to 14 carbon atoms, and $R^5$ is H or an alkyl, aryl, or alkaryl group containing from about 1 to about 10 carbon atoms, the total number of carbon atoms being from about 10 to about 20.

A group of compounds which provides the above peroxyacids are the magnesium salts of the peroxyacids of the following general formulas:

$$\left[R^1-\underset{\underset{O}{\|}}{C}-\underset{\underset{R^5}{|}}{N}-R^2-\underset{\underset{O}{\|}}{C}-OO-\right]_n^- Mg^{2+}X_{2-n} \cdot YH_2O$$

or $$\left[R^1-\underset{\underset{R^5}{|}}{N}-\underset{\underset{O}{\|}}{C}-R^2-\underset{\underset{O}{\|}}{C}-OO-\right]_n^- Mg^{2+}X_{2-n} \cdot YH_2O$$

wherein $R^1$, $R^2$ and $R^5$ are as defined for the peroxyacid, X is a compatible anion, n is one or two, and Y is from 0 to about 6.

The peroxyacids can also be formed in situ from a peroxygen bleaching compound capable of yielding hydrogen peroxide in aqueous solution and a bleach activator of the following formulas:

$$R^1-\underset{\underset{O}{\|}}{C}-\underset{\underset{R^5}{|}}{N}-R^2-\underset{\underset{O}{\|}}{C}-L \text{ or } R^1-\underset{\underset{R^5}{|}}{N}-\underset{\underset{O}{\|}}{C}-R^2-\underset{\underset{O}{\|}}{C}-L$$

wherein $R^1$, $R^2$ and $R^5$ are as defined for the peroxyacid, and L is a leaving group.

The invention also relates to bleaching compositions which contain one of the above compounds. Where the composition contains the bleach activator, another essential component is a peroxygen bleaching compound capable of yielding hydrogen peroxide in aqueous solution. In a preferred embodiment, the bleaching compositions are incorporated into detergent compositions.

DETAILED DESCRIPTION OF THE INVENTION

The invention relates to bleaching compounds which provide amide substituted peroxyacids of the following general formula:

$$R^1-\underset{\underset{O}{\|}}{C}-\underset{\underset{R^5}{|}}{N}-R^2-\underset{\underset{O}{\|}}{C}-OOH \text{ or } R^1-\underset{\underset{R^5}{|}}{N}-\underset{\underset{O}{\|}}{C}-R^2-\underset{\underset{O}{\|}}{C}-OOH$$

wherein each $R^1$ is an alkyl, aryl or alkaryl group with from about 1 to about 14 carbon atoms, $R^2$ is an alkylene group containing from about 2 to about 14 carbon atoms and at least one double bond which is alpha, beta to either one or both of the percarbonyl group and the amide carbonyl group, and $R^5$ is H or an alkyl, aryl, or alkaryl group containing 1 to 10 carbon atoms, the total number of carbon atoms being from about 8 to about 24, preferably from about 10 to about 20. $R^1$ preferably contains from about 6 to about 12 carbon atoms. $R^2$ preferably contains from about 2 to about 8 carbon atoms. $R^1$ can be straight chain or branched alkyl, substituted aryl or alkylaryl containing branching, substitution, or both. Analagous structural variations are permissible for $R^2$. The substitution can include alkyl, aryl, halogen, nitrogen, sulfur, and other typical substituent groups of organic compounds. $R^5$ preferably H or methyl. $R^1$ and $R^5$ should not contain more than 18 carbon atoms total. The $$-\underset{\underset{O}{\|}}{C}-R^2-\underset{\underset{O}{\|}}{C}-OOH$$

group in most instances is most preferably the trans form, e.g., when $R^2$ is —CH=CH— the preferred form is fumaric acid. The cis form, e.g., maleic acid, in general has a much lower melting point.

The bleaching compounds of the invention provide effective and efficient surface bleaching of textiles which thereby removes stains and/or soils from the textiles. The compounds are particularly efficient at removing dingy soils from textiles. Dingy soils are those that build up on textiles after much usage and washing, and result in a gray or yellow tint on a white textile. These soils are a blend of particulate and greasy materials.

The compounds of the invention provide effective bleaching over a wide range of temperature (5° C. to 85° C.), a preferred range being from about 30° C. to about 60° C.

The presence of the polar amide or substituted amide moiety results in a peroxyacid which has a very low vapor pressure and thus possesses a low odor profile as well as an excellent bleaching performance. Monoperoxyfumaric monoamides of amines containing from about 4 to about 18 carbon atoms, preferably from about 6 to about 12 carbon atoms are preferred.

The peroxyacid can be used directly as a bleaching agent. The improved thermal stability of the peroxyacids of the invention, especially when incorporated into the bleaching compositions and detergent compositions described hereinafter is surprising, especially when compared to alkyl peroxyacids, especially the short chain peroxyacids of the prior art, e.g. U.S. Pat. No.

4,412,934, Chung et al, incorporated herein by reference.

While not wishing to be bound by theory, it is believed that the polarity of the amide group and the unsaturated $R^2$ group result in a reduction of vapor pressure of the peroxyacid, and a corresponding increase in melting point. It is believed that increasing melting point increases the stability of the peroxyacid.

The substituted amide containing peroxyacids also have a reduced vapor pressure, and show good odor profiles. These compounds are well suited for use in the bleach activator structures provided hereinafter.

The Magnesium Peroxycarboxylate

The magnesium salt has the following general formulas:

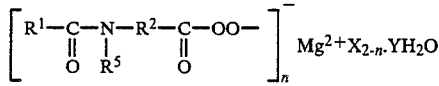

or

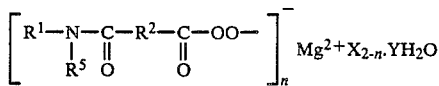

wherein $R^1$, $R^2$ and $R^5$ are as defined for the peroxyacid, X is a compatible anion, n is 1 or 2, and Y is from 0 to about 6.

The compounds are solid and possess good storage under alkaline conditions such as when admixed with a detergent composition. The active oxygen in the magnesium peroxycarboxylate is readily available. This means that the solid magnesium peroxycarboxylates are readily soluble or dispersible and yield solutions containing peroxyacids. When the solution is aqueous, it cannot be distinguished from an aqueous solution prepared from the corresponding peroxyacid and an equivalent amount of magnesium, when the solutions are adjusted to the same pH.

It is believed that the stability of the magnesium salt is due to the fact that the active oxygen atom is nucleophilic rather than electrophilic as it is in the corresponding peroxycarboxylic acid. Nucleophilic agents which would attack an electrophilic oxygen are much more prevalent in bleaching and detergent compositions than electrophilic agents.

The magnesium peroxycarboxylates can be prepared via the process of U.S. Pat. No. 4,483,781, Hartman, issued Nov. 20, 1984, incorporated herein by reference.

The Bleach Activator

The bleach activators within the invention are amide substituted compounds of the general formulas:

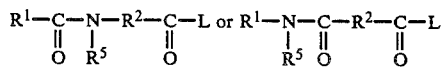

wherein $R^1$, $R^2$ and $R^5$ are as defined for the peroxyacid, and L can be essentially any suitable leaving group. A leaving group is any group that is displaced from the bleach activator as a consequence of the nucleophilic attack on the bleach activator by the perhydroxide anion. This, the perhydrolysis reaction, results in the formation of the peroxycarboxylic acid. Generally, for a group to be a suitable leaving group it must exert an electron attracting effect. It should also form a stable entity so that the rate of the back reaction is negligible. This facilitates the nucleophilic attack by the perhydroxide anion.

The L group must be sufficiently reactive for the reaction to occur within the optimum time frame (e.g., a wash cycle). However, if L is too reactive, this activator will be difficult to stabilize for use in a bleaching composition. These characteristics are generally paralleled by the pKa of the conjugate acid of the leaving group, although exceptions to this convention are known. Ordinarily, leaving groups that exhibit such behavior are those in which their conjugate acid has a pKa in the range of from about 4 to about 13, preferably from about 6 to about 11 and most preferably from about 8 to about 11.

Preferred bleach activators are those of the above general formula wherein $R^1$, $R^2$ and $R^5$ are as defined for the peroxyacid and L is selected from the group consisting of:

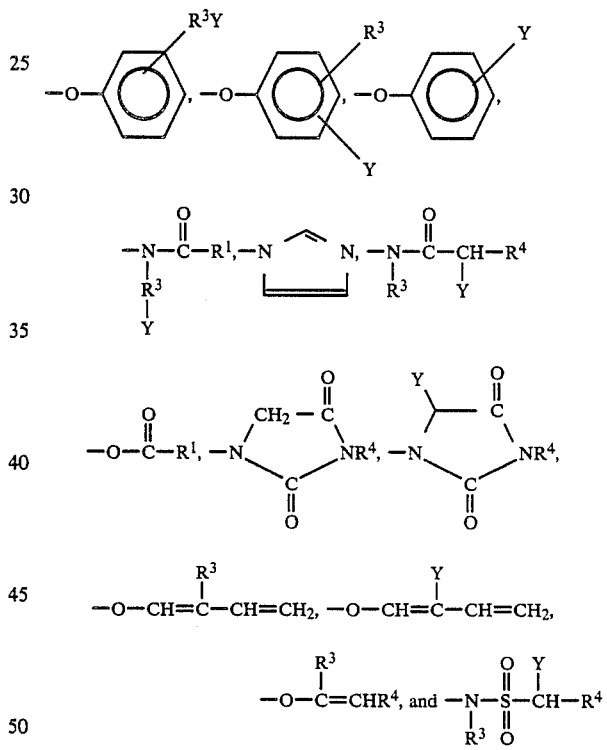

wherein $R^1$ is as defined for the peroxyacid, $R^3$ is an alkyl chain containing from about 1 to about 8 carbon atoms, $R^4$ is H or $R^3$, and Y is H or a solubilizing group. The preferred solubilizing groups are $-SO_3^-M^+$, $-COO^-M^-$, $-SO_4^-M^+$, $(-N^+R_3^3)X^-$ and $O \leftarrow N(R_3^3)-$ and most preferably $-SO_3^-M^+$ and $-COO^-M^+$ wherein $R^3$ is an alkyl chain containing from about 1 to about 4 carbon atoms, M is a cation which provides solubility to the bleach activator and X is an anion which provides solubility to the bleach activator. Preferably, M is an alkali metal, ammonium or substituted ammonium cation, with sodium and potassium being most preferred, and X is a halide, hydroxide, methylsulfate or acetate anion. It should be noted that bleach activators with a leaving group that does not contain a solubilizing group should be well dispersed in the bleaching solution in order to assist in their dissolution.

Preferred bleach activators are those wherein L is a leaving group as previously defined, $R^1$ is an alkyl group containing from about 6 to about 12 carbon atoms, $R^2$ is an alkylene group containing from about 2 carbon atoms to about 8 carbon atoms, and $R^5$ is H or methyl.

Preferred bleach activators are those of the above general formula wherein each $R^1$ is an alkyl group containing from about 6 to about 10 carbon atoms and each $R^2$ is an alkylene group containing from about 2 to about 4 carbon atoms, $R^5$ is H, and L is selected from the group consisting of:

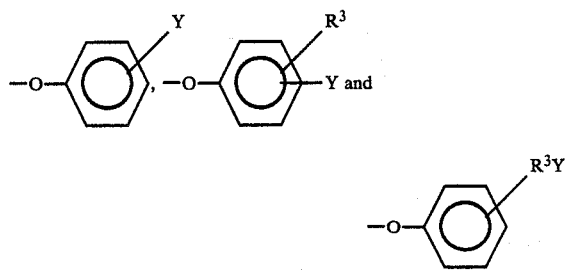

wherein $R^3$ is as defined above and Y is $-SO_3^-M^+$ or $-COO^-M^+$ wherein M is as defined above.

Especially preferred bleach activators are those wherein $R^1$ is a linear alkyl chain containing from about 6 to about 10 carbon atoms, $R^2$ is $-CH=CH-$, $R^5$ is H, and L is selected from the group consisting of:

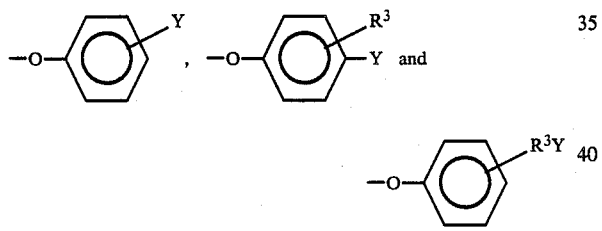

wherein $R^3$ is as defined above and Y is $-SO_3^-M^+$ or $-COO^-{}^M{}^+$ wherein M is as defined above.

The Bleaching Compositions

The bleaching compositions of the invention are those which, upon dissolution in aqueous solution, provide a bleaching compound of the formula

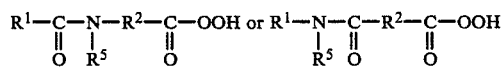

wherein $R^1$, $R^2$ and $R^5$ are as defined for the peroxyacid.

Such compositions provide extremely effective and efficient surface bleaching of textiles which thereby remove stains and/or soils from the textiles. The compositions are particularly effective at removing dingy soils from textiles. Dingy soils are soils that build up on textiles after numerous cycles of usage and washing, and thus, result in a white textile having a gray or yellow tint. These soils tend to be blend of particulate and greasy materials. The removal of this type of soil is sometimes referred to as "dingy fabric clean up".

The bleaching compositions provide such bleaching over a wide range of bleach solution temperatures. Such bleaching is obtained in bleach solutions wherein the solution temperature is at least about 5° C. Inorganic peroxygen bleaches would be ineffective and/or impracticable at temperatures below about 60° C.

This invention also relates to bleaching compositions containing a peroxygen bleach capable of releasing hydrogen peroxide in an aqueous solution and specific bleach activators, hereinafter defined, at specific molar ratios of hydrogen peroxide to bleach activator.

The bleaching mechanism generally, and the surface bleaching mechanism in particular, are not completely understood. However, it is generally believed that the bleach activator undergoes nucleophilic attack by a perhydroxide anion, which is generated from the hydrogen peroxide evolved by the peroxygen bleach, to form a peroxycarboxylic acid. This reaction is commonly referred to as perhydrolysis.

When the activators are used, optimum surface bleaching performance is obtained with bleaching solutions wherein the pH of such solution is between about 8.5 and 10.5 and preferably between 9.5 and 10.5 in order to facilitate the perhydrolysis reaction. Such pH can be obtained with substances commonly known as buffering agents, which are optional components of the bleaching compositions herein.

It is also believed, that the bleach activators within the invention can render peroxygen bleaches more efficient even at bleach solution temperatures wherein bleach activators are not necessary to activate the bleach, i.e., above about 60° C. Therefore, with bleach compositions of the invention, less peroxygen bleach is required to get the same level of surface bleaching performance as is obtained with the peroxygen bleach alone.

The bleaching compositions wherein the bleach activator is used also have, as an essential component a peroxygen bleach capable of releasing hydrogen peroxide in aqueous solution.

The Peroxygen Bleaching Compound

The peroxygen bleaching compounds useful herein are those capable of yielding hydrogen peroxide in an aqueous solution. These compounds are well known in the art and include hydrogen peroxide and the alkali metal peroxides, organic peroxide bleaching compounds such as urea peroxide, and inorganic persalt bleaching compounds, such as the alkali metal perborates, percarbonates, perphosphates, and the like. Mixtures of two or more such bleaching compounds can also be used, if desired.

Preferred peroxygen bleaching compounds include sodium perborate, commercially available in the form of mono-, tri- and tetra-hydrate, sodium carbonate peroxyhydrate, sodium pyrophosphate peroxyhydrate, urea peroxyhydrate, and sodium peroxide. Particularly preferred are sodium perborate tetrahydrate and, especially, sodium perborate monohydrate. Sodium perborate monohydrate is especially preferred because it is very stable during storage and yet still dissolves very quickly in the bleaching solution. It is believed that such rapid dissolution results in the formation of higher levels of percarboxylic acid and, thus, enhanced surface bleaching performance.

The level of bleach activator within the compositions of the invention is from about 0.1% to about 60% and preferably from about 0.5% to about 40%. When the bleaching compositions within the invention are also detergent compositions it is preferred that the level of bleach activator is from about 0.5% to about 20%.

Optional Components

As a preferred embodiment, the bleaching compositions of the invention can be detergent compositions. Thus, the bleaching compositions can contain typical detergent composition components such as detergency surfactants and detergency builders. In such preferred embodiments the bleaching compositions are particularly effective. The bleaching compositions of this invention can contain all of the usual components of detergent compositions including the ingredients set forth in U.S. Pat. No. 3,936,537, Baskerville et al, incorporated herein by reference. Such components include color speckles, suds boosters, suds suppressors, antitarnish and/or anticorrosion agents, soil-suspending agents, soil-release agents, dyes, fillers, optical brighteners, germicides, alkalinity sources, hydrotropes, antioxidants, enzymes, enzyme stabilizing agents, perfumes, etc.

Enzymes are highly preferred optional ingredients and are incorporated in an amount of from about 0.025% to about 5%, preferably from about 0.05% to about 1.5%. A proteolytic activity of from about 0.01 to about 0.05 Anson units per gram of product is desirable. Other enzymes, including amylolytic enzymes, are also desirably included in the present compositions.

Suitable proteolytic enzymes include the many species known to be adapted for use in detergent compositions. Commercial enzyme preparations such as "Alcalase" and "Savinase", sold by Novo Industries, and "Maxatase" sold by Gist-Brocades, Delft, The Netherlands, are suitable. Other preferred enzyme compositions include those commercially available under the tradenames SP-72 ("Esperase") manufactured and sold by Novo Industries, A/S, Copenhagen, Denmark and "AZ-Protease" manufactured and sold by Gist-Brocades, Delft, The Netherlands.

Suitable amylases include "Rapidase" sold by Gist-Brocades and "Termamyl" sold by Novo Industries.

A more complete disclosure of suitable enzymes can be found in U.S. Pat. No. 4,101,457, Place et al, issued July 18, 1978, incorporated heren by reference.

The detergent surfactants can be any one or more surface active agents selected from anionic, nonionic, zwitterionic, amphoteric and cationic classes and compatible mixtures thereof. Detergent surfactants useful herein are listed in U.S. Pat. No. 3,664,961, Norris, issued May 23, 1972, and in U.S. Pat. No. 3,919,678, Laughlin et al, issued Dec. 30, 1975, both incorporated herein by reference. Useful cationic surfactants also include those described in U.S. Pat. No. 4,222,905, Cockrell, issued Sept. 16, 1980, and in U.S. Pat. No. 4,239,659, Murphy, issued Dec. 16, 1980, both incorporated herein by reference. The following are representative examples of detergent surfactants useful in the present compositions.

Water-soluble salts of the higher fatty acids, i.e., "soaps", are useful anionic surfactants in the compositions herein. This includes alkali metal soaps such as the sodium, potassium, ammonium, and alkylolammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Useful anionic surfactants also include the water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are the sodium and potassium alkyl sulfates, especially those obtained by sulfating the higher alcohols ($C_8$–$C_{18}$ carbon atoms) such as those produced by reducing the glycerides of tallow or coconut oil; and the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11-13}$LAS.

Other anionic surfactants herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 10 units of ethylene oxide per molecule and wherein the alkyl group contains from about 10 to about 20 carbon atoms.

Other useful anionic surfactants herein include the water-soluble salts of esters of alpha-sulfonated fatty acids containing from about 6 to 20 carbon atoms in the fatty acid group and from about 1 to 10 carbon atoms in the ester group; water-soluble salts of 2-acyloxyalkane-1-sulfonic acids containing from about 2 to 9 carbon atoms in the acyl group and from about 9 to about 23 carbon atoms in the alkane moiety; water-soluble salts of olefin and paraffin sulfonates containing from about 12 to 20 carbon atoms; and beta-alkyloxy alkane sulfonates containing from about 1 to 3 carbon atoms in the alkyl group and from about 8 to 20 carbon atoms in the alkane moiety.

Water-soluble nonionic surfactants are also useful in the compositions of the invention. Such nonionic materials include compounds produced by the condensation of alkylene oxide groups (hydrophilic in nature) with an organic hydrophobic compound, which may be aliphatic or alkyl aromatic in nature. The length of the polyoxyalkylene group which is condensed with any particular hydrophobic group can be readily adjusted to yield a water-soluble compound having the desired degree of balance between hydrophilic and hydrophobic elements.

Suitable nonionic surfactants include the polyethylene oxide condensates of alkyl phenols, e.g., the condensation products of alkyl phenols having an alkyl group containing from about 6 to 15 carbon atoms, in either a straight chain or branched chain configuration, with from about 3 to 12 moles of ethylene oxide per mole of alkyl phenol.

Preferred nonionics are the water-soluble and water-dispersible condensation products of aliphatic alcohols containing from 8 to 22 carbon atoms, in either straight chain or branched configuration, with from 3 to 12 moles of ethylene oxide per mole of alcohol. Particularly preferred are the condensation products of alcohols having an alkyl group containing from about 9 to 15 carbon atoms with from about 4 to 8 moles of ethylene oxide per mole of alcohol.

Semi-polar nonionic surfactants include water-soluble amine oxides containing one alkyl moiety of from about 10 to 18 carbon atoms and two moieties selected from the group of alkyl and hydroxyalkyl moieties of from about 1 to about 3 carbon atoms; water-soluble phosphine oxides containing one alkyl moiety of about 10 to 18 carbon atoms and two moieties selected from the group consisting of alkyl groups and hydroxyalkyl groups containing from about 1 to 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Ampholytic surfactants include derivatives of aliphatic or aliphatic derivatives of heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic surfactants include derivatives of aliphatic, quaternary, ammonium, phosphonium, and sulfonium compounds in which one of the aliphatic substituents contains from about 8 to 18 carbon atoms.

The level of detergent surfactant that can be employed is from 0% to about 50%, preferably from about 1% to about 30% and most preferably from about 10% to about 25% by weight of the total composition.

In addition to detergent surfactants, detergency builders can be employed in the bleaching compositions. Water-soluble inorganic or organic electrolytes are suitable builders. The builder can also be water-insoluble calcium ion exchange materials; nonlimiting examples of suitable water-soluble, inorganic detergent builders include: alkali metal carbonates, borates, phosphates, bicarbonates and silicates. Specific examples of such salts include sodium and potassium tetraborates, bicarbonates, carbonates, orthophosphates, pyrophosphates, tripolyphosphates and metaphosphates.

Examples of suitable organic alkaline detergency builders include: (1) water-soluble amino carboxylates and aminopolyacetates, for example, nitrilotriacetates, glycinates, ethylenediaminetetraacetates, N-(2-hydroxyethyl)nitrilodiacetates and diethylenetriaminepentaacetates; (2) water-soluble salts of phytic acid, for example, sodium and potassium phytates; (3) water-soluble polyphosphonates, including sodium, potassium, and lithium salts of ethane-1-hydroxy-1,1-diphosphonic acid; sodium, potassium, and lithium salts of ethylene diphosphonic acid; and the like; (4) water-soluble polycarboxylates such as the salts of lactic acid, succinic acid, malonic acid, maleic acid, citric acid, carboxymethyloxysuccinic acid, 2-oxa-1,1,3-propane tricarboxylic acid, 1,1,2,2-ethane tetracarboxylic acid, mellitic acid and pyromellitic acid; and (5) water-soluble polyacetals as disclosed in U.S. Pat. Nos. 4,144,266 and 4,246,495 incorporated herein by reference.

Another type of detergency builder material useful in the present compositions comprises a water-soluble material capable of forming a water-insoluble reaction product with water hardness cations preferably in combination with a crystallization seed which is capable of providing growth sites for said reaction product. Such "seeded builder" compositions are fully disclosed in British Patent Specification No. 1,424,406.

A further class of detergency builder materials useful in the present invention are insoluble sodium aluminosilicates, particularly those described in U.S. Pat. No. 4,605,509, Corkill et al, issued Aug. 12, 1986, incorporated herein by reference. This patent discloses and claims detergent compositions containing sodium aluminosilicates having the formula:

$$Na_z(AlO_2)_z(SiO_2)_y \cdot XH_2O$$

wherein z and y are integers equal to at least 6, the molar ratio of z to y is in the range of from 1.0:1 to about 0.5:1, and X is an integer from about 15 to about 264, said aluminosilicates having a calcium ion exchange capacity of at least 200 milligrams equivalent/gram and a calcium ion exchange rate of at least about 2 grains/gallon/minute/gram. A preferred material is Zeolite A which is:

$$Na_{12}(SiO_2AlO_2)_{12} \cdot 27H_2O$$

The level of detergency builder of the bleaching compositions is from 0% to about 70%, preferably from about 10% to about 60% and most preferably from about 20% to about 60%.

Buffering agents can be utilized to maintain the desired alkaline pH of the bleaching solutions. Buffering agents include, but are not limited to many of the detergency builder compounds disclosed hereinbefore. Buffering agents suitable for use herein are those well known in the detergency art.

Preferred optional ingredients include suds modifiers particularly those of suds suppressing types, exemplified by silicones, and silica-silicone mixtures.

U.S. Pat. Nos. 3,933,672, issued Jan. 20, 1976 to Bartolotta et al, and 4,136,045, issued Jan. 23, 1979 to Gault et al, incorporated herein by reference, disclose silicone suds controlling agents. The silicone material can be represented by alkylated polysiloxane materials such as silica aerogels and xerogels and hydrophobic silicas of various types. The silicone material can be described as siloxane having the formula:

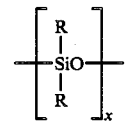

wherein x is from about 20 to about 2,000 and each R is an alkyl or aryl group, especially methyl, ethyl, propyl, butyl and phenyl groups. The polydimethylsiloxanes (both Rs are methyl) having a molecular weight within the range of from about 200 to about 2,000,000, and higher, are all useful as suds controlling agents. Additional suitable silicone materials wherein the side chain groups R are alkyl, aryl, or mixed alkyl or aryl hydrocarbyl groups exhibit useful suds controlling properties. Examples of the like ingredients include diethyl-, dipropyl-, dibutyl-, methyl-, ethyl-, phenylmethylpoly-siloxanes and the like. Additional useful silicone suds controlling agents can be represented by a mixture of an alkylated siloxane, as referred to hereinbefore, and solid silica. Such mixtures are prepared by affixing the silicone to the surface of the solid silica. A preferred silicone suds controlling agent is represented by a hydrophobic silanated (most preferably trimethylsilanated) silica having a particle size in the range from about 10 millimicrons to 20 millimicrons and a specific surface area above about 50 m²/gm. intimately admixed with dimethyl silicone fluid having a molecular weight in the range from about 500 to about 200,000 at a weight ratio of silicone to silanated silica of from about 19:1 to about 1:2. The silicone suds suppressing agent is advantageously releasably incorporated in a water-soluble or water-dispersible, substantially non-surface-active detergent-impermeable carrier.

Particularly useful suds suppressors are the self-emulsifying silicone suds suppressors, described in U.S. Pat. No. 4,073,118, Gault et al, issued Feb. 21, 1978, incorporated herein by reference. An example of such a compound is DB-544, commercially available from Dow Corning, which is a siloxane/glycol copolymer.

Suds modifiers as described above are used at levels of up to approximately 2%, preferably from about 0.1 to about 1½% by weight of the surfactant.

Microcrystalline waxes having a melting point in the range from 35° C.-115° C. and a saponification value of less than 100 represent additional examples of preferred suds control components for use in the subject compositions, and are described in detail in U.S. Pat. No. 4,056,481, Tate, issued Nov. 1, 1977, incorporated herein by reference. The microcrystalline waxes are substantially water-insoluble, but are water-dispersible in the presence of organic surfactants. Preferred microcrystalline waxes have a melting point from about 65° C. to 100° C., a molecular weight in the range from 400–1,000; and a penetration value of at least 6, measured at 77° F. by ASTM-D1321. Suitable examples of the above waxes include: microcrystalline and oxidized microcrystalline petroleum waxes; Fischer-Tropsch and oxidized Fischer-Tropsch waxes; ozokerite; ceresin; montan wax; beeswax; candelilla; and carnauba wax.

Alkyl phosphate esters represent an additional preferred suds control agent for use herein. These preferred phosphate esters are predominantly monostearyl phosphate which, in addition thereto, can contain di- and tristearyl phosphates and monooleyl phosphate, which can contain di- and trioleyl phosphate.

Other suds control agents useful in the practice of the invention are the soap or the soap and nonionic mixtures as disclosed in U.S. Pat. Nos. 2,954,347 and 2,954,348, incorporated herein by reference.

This invention also relates to the process of bleaching textiles with a compound which, when in aqueous solution, yields a peroxyacid of the following formulas:

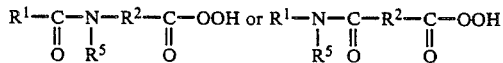

wherein $R^1$, $R^2$ and $R^5$ are as defined hereinbefore.

The following examples are given to illustrate the parameters of and compositions within the invention. All percentages, parts and ratios are by weight unless otherwise indicated.

EXAMPLE 1

Preparation of the Monononylamide of Monperoxyfumaric Acid

A. Mixed Ethyl Ester/Acid Chloride of Fumaric Acid

Fumaric acid, monoethyl ester (50.0 g, 0.347 mol) and 40 ml (65.2 g, 0.548 mol) of thionyl chloride were charged into a 250 mL round-bottom flask. The flask was fitted with a reflux condenser and drying tube. A boiling chip was added and the reaction mixture was heated in a 65° C. water bath for 3.5 hr. At the end of this period evolution of acidic gases had ceased and the reaction mixture was a yellow liquid. Heptane (50 mL) was added and the exess thionyl chloride removed on a rotary evaporator. The process of adding heptane (50 mL) and stripping on a rotary evaporator was repeated two additional times, yielding 58.0 g of the mixed ethyl ester/acid choride as a dark-yellow oil.

B. Mixed Ethyl Ester/Nonyl Amide of Fumaric Acid

A one liter beaker fitted with a mechanical stirrer and pH electrode was charged with 350 mL of water and 49.7 g (0.347 mol) of nonyl amine dissolved in 100 mL ether. The resulting mixture was cooled in an ice bath and, with stirring, a solution in 100 ml ether of the mixed ethyl ester/acid chloride obtained above was added dropwise over a 30 minute period. Concurrent with addition of the ethyl ester/acid chloride was added 50% sodium hydroxide solution at a rate so as to maintain the pH of the aqueous layer between 10 and 12. Following addition the ice bath was removed and the mixture allowed to stand one hour at room temperature. The precipitate tan solid was extracted into 250 ml methylene chloride, the methylene chloride layer separated, and the aqueous layer extracted with 50 mL methylene chloride. The combined methylene chloride solutions were washed with saturated sodium chloride solution, dried over magnesium sulfate, and stripped on a rotary evaporator to yield 82.9 g of a yellow-orange oil. This oil was crystallized from 400 mL of hexane to yield 54.0 g of white solid, mp 52°-56° C. This solid was recrystallized from hexane to give 51.1 g of the mixed ethyl ester/nonyl amide of fumaric acid as a white solid, mp 50°-54° C.

C. Monononylamide of Monoperoxyfumaric Acid

The mixed ethyl ester/nonyl amide of fumaric acid (obtained above, 25.0 g, 0.0928 mol) was dissolved in 50 mL of methanesulfonic acid. The resulting solution was cooled in an ice bath and, with stirring, 22.6 g (0.464 mol) of 70% hydrogen peroxide was added dropwise at a rate such as to maintain the reaction temperature below 20° C. Addition of the peroxide required 15 minutes. The ice bath was removed and the reaction mixture allowed to stir at room temperature for 1.5 hours. The reaction mixture was poured over ice and the precipitated solid collected by filtration and washed with water. The resulting filter cake was mixed with 150 mL ethyl acetate at 65° C., resulting in two clear layers. The lower aqueous layer was removed via a pipet and the upper ethyl acetate layer cooled to −18° C. The crystals which formed were collected by filtration and washed with −18° C. ethyl acetate. Drying afforded 17.2 g of the monononylamide of monoperoxyfumaric acid as colorless crystals, mp 123°-125° C. Analysis for available oxygen (AvO) indicated 5.78%. Theoretical yield would be 23.9 g having an available oxygen content of 6.22%.

EXAMPLE II

Stability of the Mononylamide of Monoperoxyfumaric Acid

The stability of the mononylamide of monoperoxyfumaric acid was measured as a function of temperature and humidity. Storage was as 0.2 g samples in glass jars having vented tops. The activity of the peroxyacid versus time was determined by conventional iodometric titration of the individual 0.2 g samples for available oxygen. The results shown below are for two different samples of the peroxyacid, one of which was stored only at 120° F.

| Stability of the Mononylamide of Monoperoxyfumaric Acid | | | | |
|---|---|---|---|---|
| Length of Storage (Weeks) | % of Original Activity | | | |
| | Sample A | | | Sample B |
| | 80° F. | 100° F. | 120° F. | 120° F. |
| 1 | 99 | 100 | 100 | 108 |
| 3 | 109 | 98 | 82 | 102 |
| 5 | | | | 100 |
| 7 | 100 | 93 | 75 | 100 |
| 9 | 99 | 89 | 75 | |
| 10 | | | | 102 |
| 12 | 99 | 61 | 68 | |
| 17 | | | | 97 |
| 19 | 101 | 79 | 68 | |
| 21 | | | | 100 |
| 30 | | | | 99 |
| 32 | 101 | 74 | 65 | |
| 56 | | | | 98 |
| 58 | 95 | 2 | 59 | |
| 60 | | 80 | | |
| 63 | 94 | | 66 | 71 |

EXAMPLE III

Bleaching Performance of the Mononylamide of Monoperoxyfumaric Acid

The bleaching performance of the mononylamide of monoperoxyfumaric acid was measured in a series of experiments which compared the fabric whitening and stain removal of a treatment containing the peroxyacid with one that did not contain bleach.

Thus, to each of two miniature automatic washing machines was added 7.6 liters of 95° F. water having a hardness of 5 gr/gal. To one machine was added 8.0 g of a phosphate-built heavy-duty detergent granule, 1.7 g of sodium carbonate, and 200 g of clean terry cloth to serve as ballast fabric. The pH of the resulting solution was 10.1. To a second machine was added 8.0 g of the phosphate-built detergent granule and a quantity of the mononylamide of monoperoxyfumaric acid sufficient to provide 3.5 ppm of available oxygen (AvO) in the wash solution. The pH of the resulting solution was 9.3.

To each of the above wash solutions were added naturally soiled fabrics and artificially stained swatches. The washing machines were then allowed to complete their normal washing and rinsing cycles, and the ballast and test fabrics were dryer dried. This procedure was repeated four times, using different sets of ballast fabrics, naturally soiled fabrics and artificially stained swatches for each replicate.

After completion of the four replicates the fabrics and swatches were arranged under suitable lighting for comparison of soil and stain removal. Three expert granders compared the extent of removal of the soils and stains using the following scale:

0: no difference between two swatches
1: thought to be a difference
2: certain of a difference
3: certain of a large difference
4: certain of a very large difference In this grading the naturally soiled fabrics were compared for improvement in whiteness, and the artificially stained swatches were compared for removal of the stain. The grades obtained were then averaged and normalized to yield the results shown below.

| | Treatment and Average Relative Grade | |
|---|---|---|
| | Detergent Granule + Sodium Carbonate | Detergent Granule + 3.5 ppm AvO From Mononylamide of Monoperoxyfumaric Acid |
| Naturally Soiled Fabrics | | |
| T-shirts | 0 | 1.0 s |
| Dish towels | 0 | 1.4 s |
| Pillowcase | 0 | 1.9 s |
| Stained Fabrics | | |
| Clay | 0 | −0.5 |
| Spaghetti sauce | 0 | 2.5 s |
| Barbecue sauce | 0 | 0.1 |
| Tea | 0 | 4.0 s |
| Grass | 0 | 2.4 s |
| Blueberries | 0 | 1.6 s | s = Statistically significant difference (confidence level of 90%) relative to the detergent granule + sodium carbonate treatment.

There is excellent bleaching/cleaning performance at pH's of less than about 9.5.

What is claimed is:

1. A bleaching compound which provides in an aqueous solution a compound of the formula:

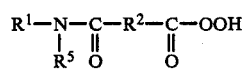

wherein each $R^1$ is an alkyl, aryl or alkaryl group containing from about 1 to about 14 carbon atoms, $R^2$ is trans —CH=CH—, and $R^5$ is H or an alkyl, aryl or alkaryl group containing from about 1 to about 10 carbon atoms, the total number of carbon atoms being from about 10 to about 20.

2. A compound according to claim 1 wherein the compound has the formula:

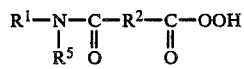

wherein $R^1$, $R^2$ and $R^5$ are as defined in claim 1.

3. A compound according to claim 1 wherein $R^1$ is an alkyl group containing from about 6 to about 12 carbon atoms, $R^2$ is trans—CH=CH—, and $R^5$ is H or methyl.

4. A compound according to claim 1 of the formula:

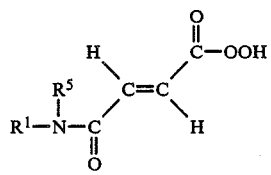

wherein $R^1$ and $R^5$ are as defined in claim 1.

5. A compound according to claim 1 wherein the compound is a magnesium peroxycarboxylate of the following general formula:

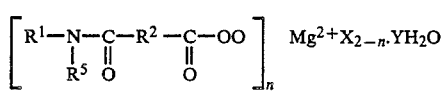

wherein $R^1$, $R^2$ and $R^5$ are as defined in claim 1, X is a compatible anion, n is 1 or 2, and Y is from 0 to about 6.

6. A compound according to claim 5 wherein $R^1$ is an alkyl group containing from about 6 to about 12 carbon atoms, $R^2$ is trans—CH=CH—, and $R^5$ is H or methyl.

7. A compound according to claim 5 of the formula:

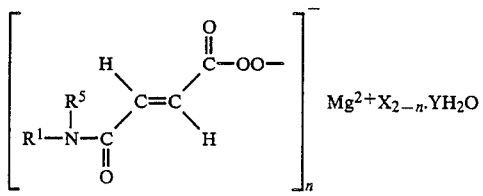

wherein $R^1$, $R^5$, n, X and Y are as defined in claim 5.

8. A bleach activator of the general formula:

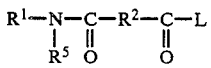

wherein $R^1$ is an alkyl, aryl or alkaryl grop containing from about 1 to about 14 carbon atoms, $R^2$ is trans—CH=CH—, and $R^5$ is H or an alkyl, aryl or alkaryl group containing from about 1 to about 10 carbon atoms, and L is a leaving group.

9. The compound of claim 8 wherein L is selected from the group consisting of:

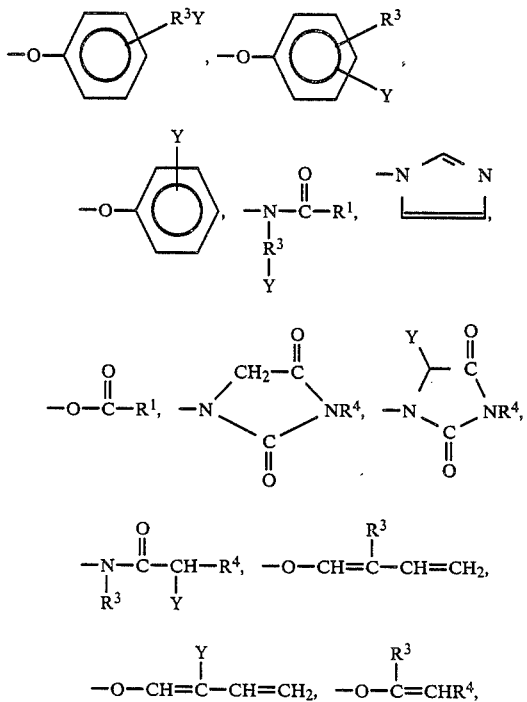

-continued

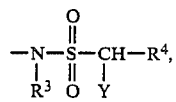

and mixtures thereof
wherein $R^1$ is as defined in claim 1, $R^3$ is an alkyl chain containing from about 1 to about 8 carbon atoms, $R^4$ is H or $R^3$, and Y is H or a solubilizing group.

10. The compound of claim 9 wherein Y is selected from the group consisting of: $-SO_3^-M^+$, $-COO^-M^+$, $-SO_4^-M^+$, $(-N^+R_3{}^3)X^-$ and $O\leftarrow N(R_2{}^3)-$ and mixtures thereof wherein $R^3$ is an alkyl chain containing from about 1 to about 4 carbon atoms, M is a cation which provides solubility to the bleach activator and X is an anion which provides solubility to the bleach activator.

11. A detergent composition comprising an effective amount of said bleaching compound of claim 1 and also comprising from about 1% to about 30% of a detergent surfactant.

12. A detergent composition according to claim 11 also comprising from about 10% to about 60% of a detergency builder.

13. A composition according to claim 8 comprising:
   (a) a peroxygen bleaching compound capable of yielding hydrogen peroxide in an aqueous solution; and
   (b) an effective amount of said bleach activator wherein the molar ratio of hydrogen peroxide yielded by (a) to bleach activator (b) is greater than about 1.0.

14. A compound according to claim 13 wherein $R^1$ is an alkyl group containing from about 6 to about 12 carbon atoms, and $R^5$ is H or methyl.

15. The compound of claim 13 wherein L is a leaving group, the conjugate acid of which has a $pK_a$ in the range of from about 6 to about 11.

16. The composition of claim 13 wherein L is selected from the group consisting of:

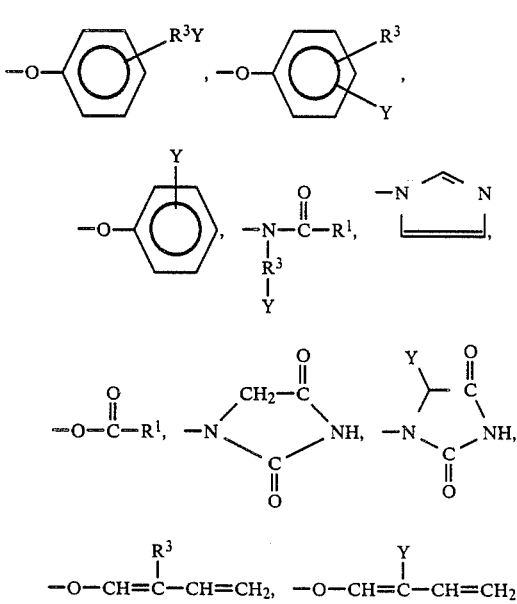

-continued

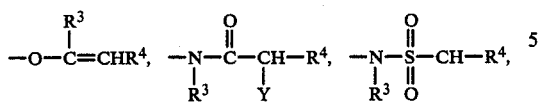

and mixtures thereof wherein $R^1$ is as defined in claim 1, $R^3$ is an alkyl chain containing from about 1 to about 8 carbon atoms, $R^4$ is H or $R^3$, and Y is H or a solubilizing group.

17. The composition of claim 14 wherein L is selected from the group consisting of:

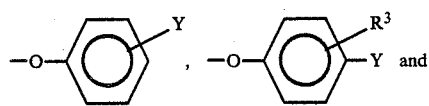

-continued

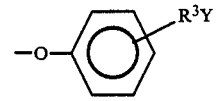

wherein $R^3$ is an alkyl chain containing from about 1 to about 8 carbon atoms, Y is $-SO_3^-M^+$ or $-COO^-M^+$ wherein M is sodium or potassium.

18. The composition of claim 17 wherein $R^1$ contains from about 1 to about 10 carbon atoms.

19. The process of bleaching textiles with a compound which in an aqueous solution can yield a peroxyacid of the general formula:

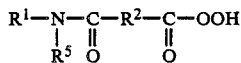

wherein each $R^1$ is an alkyl, aryl or alkaryl group containing from about 1 to about 14 carbon atoms, $R^2$ is trans $-CH=CH-$, and $R^5$ is H or an alkyl, aryl or alkaryl group containing from about 1 to about 10 carbon atoms, the total number of carbon atoms being from about 10 to about 20, comprising the step of contacting a textile with an aqueous solution containing a bleaching effective amount of said peroxyacid.

* * * * *